(12) United States Patent
Tam et al.

(10) Patent No.: US 6,423,695 B1
(45) Date of Patent: Jul. 23, 2002

(54) CYTOKINE RELATED TREATMENTS OF DISEASE

(75) Inventors: Robert Tam; Guangyi Wang; Devron Averett, all of Irvine; Kandasamy Ramasamy, Laguna Hills, all of CA (US)

(73) Assignee: Ribapharm, Inc., Costa Mesa, CA (US)

( * ) Notice: Subject to any disclaimer, the term of this patent is extended or adjusted under 35 U.S.C. 154(b) by 0 days.

(21) Appl. No.: 09/467,443

(22) Filed: Dec. 20, 1999

Related U.S. Application Data

(63) Continuation of application No. PCT/US98/00634, filed on Jan. 13, 1998.

(51) Int. Cl.⁷ .............................................. A61K 31/675

(52) U.S. Cl. ........................................................ 514/81

(58) Field of Search ............................................ 514/81

(56) References Cited

U.S. PATENT DOCUMENTS 6,063,628 A * 5/2000 Loeb et al. ................. 435/442

* cited by examiner

*Primary Examiner*—Zohreh Fay
(74) *Attorney, Agent, or Firm*—Rutan & Tucker, LLP; Robert D. Fish

(57) ABSTRACT

Nucleosides and other compounds to selectively modulate Th1 and Th2 responses relative to each other in the treatment of disease. In one aspect of the invention, administration of a nucleoside or other compound reduces the dosage at which a primary drug is administered. In another aspect of the invention, an abnormality reflected in increased response in one group of cytokines is treated by administering a nucleoside or other compound that increases response in another group of cytokines. In yet another aspect of the invention, a patient is prophylactically treated by administering a nucleoside or other compound that selectively reduces Th1 activity without significantly reducing Th2 activity. In yet another aspect of the invention, a nucleoside or other compound is administered to a patient at a dose that reduces the patient's GTP pool to a degree that selectively reduces one of the Th1 or Th2 responses without significantly reducing the other response. Controlled release dosage forms are particularly contemplated to achieve that result.

12 Claims, No Drawings

CYTOKINE RELATED TREATMENTS OF DISEASE

This application claims priority to the US National Phase Application filed Jul. 9, 1999 that claims priority to and a continuation of the International Application No: PCT/US98/00634 filed on Jan. 13, 1998.

FIELD OF THE INVENTION

The present invention relates to the field of nucleosides.

BACKGROUND OF THE INVENTION

Mammalian immune systems contain two major classes of lymphocytes: B lymphocytes (B cells), which originate in the bone marrow; and T lymphocytes (T cells) that originate in the thymus. B cells are largely responsible for humoral immunity (i.e., antibody production), while T cells are largely responsible for cell-mediated immunity.

T cells are generally considered to fall into two subclasses, helper T cells and cytotoxic T cells. Helper T cells activate other lymphocytes, including B cells and cytotoxic T cells, and macrophages, by releasing soluble protein mediators called cytokines that are involved in cell-mediated immunity. As used herein, lymphokines are a subset of cytokines.

Helper T cells are also generally considered to fall into two subclasses, Th1 and Th2. Th1 cells (also known as Type 1 cells) produce interleukin 2 (IL–2), tumor necrosis factor (TNFα) and interferon gamma (IFNγ), and are responsible primarily for cell-mediated immunity such as delayed type hypersensitivity and antiviral immunity. In contrast, Th2 cells (also known as Type 2 cells) produce interleukins, IL4,IL–5,IL–6, IL–9,IL–10 and IL–1 3,and are primarily involved in assisting humoral immune responses such as those seen in response to allergens, e.g. IgE and IgG4 antibody isotype switching (Mosmann, 1989,*Annu Rev Immunol*, 7:145–173).

As used herein, the terms Th1 and Th2 "responses",are meant to include the entire range of effects resulting from induction of Th1 and Th2 lymphocytes, respectively. Among other things, such responses include variation in production of the corresponding cytokines through transcription, translation, secretion and possibly other mechanisms, increased proliferation of the corresponding lymphocytes, and other effects associated with increased production of cytokines, including motility effects.

The priority applications, each of which is incorporated herein by reference, relate to aspects of our recent discoveries involving the effect of various nucleosides (which are defined herein to include derivatives and analogs of native nucleosides) on selectively modulating lymphocyte responses relative to each other. Among other things, we have shown that either of Th1 and Th2 responses can be selectively suppressed while the other is either induced or left relatively unaffected, and either of Th 1 or Th2 responses can be selectively induced while the other is either suppressed or left relatively unaffected. We have also discovered the surprising fact that nucleosides effective in selectively modulating Th1 and Th2 responses relative to one another tend to have a bimodal effect. Among other things, nucleosides that tend to generally suppress or induce both Th1 and Th1 activity at a relatively higher dose. tend to selectively modulate Th1 and Th2 relative to each other at relatively lower doses.

The mechanisms by which nucleosides and other compounds selectively modulate Th1 and Th2 responses relative to each other are still unclear. One possibility contemplated by the present inventors is that effective nucleosides alter the pool of guanosine triphosphate (GTP), which in turn affects the rate at which cytokines are produced. In this theory, relatively large variations in available GTP are sufficient to affect concentrations of both Th1 and Th2 cytokines, while relatively smaller variations in available GTP tend to affect concentrations of Th1 and Th2 cytokines to different extents.

The effects of 2-β-D-ribofuranosylthiazole-4-carboxamide (Tiazofurin), a synthetic C-nucleoside analogue, on GTP levels supports this view. Tumor cells are characterized by high levels of inosine monophosphate dehydrogenase (IMP DH) activity, and it is known that IMP DH is the rate-limiting enzyme of GTP biosynthesis. Weber, G., *IMP Dehydrogenase and GTP as Targets in Human Leukemia Treatment*. Adv. Exp. Med. Biol. 309B:287–292 (1991). Tiazofurin has been shown to selectively block IMP DH activity and deplete guanine nucleotide pools, which in turn forces various tumors into remission. Weber, G., *Critical Issues in Chemotherapy with Tiazofurin*, Adv. Enzyme Regul. 29:75–95 (1989). Typical initial doses of Tiazofurin are about 4,400 mg/m$^2$, with consolidation doses of about 1100 to 3300 mg/m$^2$. At these levels synthesis of both Th1 and Th2 responses are greatly reduced, thereby essentially shutting down much of the immune system. In one aspect of the present invention it is contemplated that much smaller doses of Tiazofurin, in the range of 1/10th to one-half that set forth above, would be sufficient to specifically suppress either a Th1 response or a Th2 response without greatly reducing the other response.

The effects of 1β-D-ribofuranosyl-1,2,4-triazole-3-carboxamide (Ribavirin) also supports the present theory. Ribavirin is a potent, broad-spectrum antiviral agent, which has also been shown to inhibit IMP DH. Yamada, Y. et al., *Action of the Active Metabolites of Tiazofurin and Ribavirin on Purified IMP Dehydrogenase*, Biochem. 27:2193–2196 (1988). Ribavirin proceeds under a different mechanism than Tiazofurin in inhibiting IMP DH, however, acting on a different site on the enzyme molecule. Ribavirin is converted to its active metabolite, ribavirin-monophosphate (RMP), which inhibits the enzyme at the IMP-XMP site of IMP DH. As with Tiazofurin, the affinity of Ribavirin's active form to the enzyme is higher than that of the natural metabolite. At relatively high doses, approximately 2200 mg/m$^2$ or about 1200–1500 mg/day for an adult, Ribavirin reduces IMP DH activity to such an extent that both Th1 and Th2 responses are inhibited. At relatively lower dosages of approximately 600 to 1000 mg/day, Ribavirin promotes a Th1 response and suppresses a Th2 response.

Despite the existence of as-yet undefined mechanisms, we have discovered that enormous potential benefits can be derived from selective modulation of Th1 and Th2 responses relative to each other. We have concluded, for example, that specific modulation of Th1 relative to Th2 can be useful in treating a wide variety of conditions and diseases, ranging from infections, infestations, tumors and hypersensitivities to autoimmune diseases.

These discoveries are especially significant because modern treatment strategies for many of the above-listed diseases have limited effectiveness, significant side effects, or both. Treatment of autoimmune disease, for example, is frequently limited to palliative measures, removal of toxic antibodies (as in myasthenia gravis), and administration of hazardous drugs including corticosteroids, chloroquine derivatives, and antimetabolic or antitumor drugs, and drugs such as cyclosporines that target immune system cells.

SUMMARY OF THE INVENTION

This application relates to the use of monocyclic nucleosides in a relatively low dosage range to selectively modulate Th1 and Th2 responses relative to each other in the treatment of disease. In one aspect of the invention, administration of a nucleoside or other compound reduces the dosage at which a primary drug is administered. In another aspect of the invention, an abnormality reflected in increased response in one group of cytokines is treated by administering a nucleoside or other compound that increases response in another group of cytokines. In yet another aspect of the invention, a patient is prophylactically treated by administering a nucleoside or other compound that selectively reduces Th1 activity without significantly reducing Th2 activity. In yet another aspect of the invention, a nucleoside or other compound is administered to a patient at a dose that reduces the patient's GTP pool to a degree that selectively reduces one of the Th1 or Th2 responses without significantly reducing the other response. Controlled release dosage forms are particularly contemplated to achieve that result.

Examples of nucleosides contemplated to be effective in this manner are D- and L-forms of monocyclic nucleosides corresponding to Formula 1.

Examples of primary drugs contemplated to be effective in this manner are anti-viral agents such as Ribavirin, acyclovir, and AZT™; anti-fungal agents such as tolnaftate, Fungizone™, Lotrimin™, Mycelex™, Nystatin and Amphoteracin; anti-parasitics such as Mintezol™, Niclocide™, Vermox™, and Flagyl™; bowel agents such as Immodium™, Lomotil™ and Phazyme™; anti-tumor agents such as Adriamycin™, Cytoxan™, Imuran™, Methotrxate, Mithracin™, Tiazofurin™, Taxol™; dermatologic agents such as Aclovate™, Cyclocort™, Denorex, Florone™, Oxsoralen™, coal tar and salicylic acid; migraine preparations such as ergotamine compounds; steroids and immunosuppresants not listed above, including cyclosporins, Diprosone™, hydrocortisone; Floron™, Lidex™, Topicort and Valisone; and metabolic agents such as insulin.

DETAILED DESCRIPTION

The terms "α" and "β" indicate the specific stereochemical configuration of a substituent at an asymmetric carbon atom in a chemical structure as drawn.

The term "abnormality" refers to a condition associated with a disease. Thus, Th1 and/or Th2 responses resulting from an autoimmune disease are considered herein to be abnormalities of the corresponding cytokine(s) even though such cytokine responses may commonly result from the disease.

The term "aryl" refers to a monovalent unsaturated aromatic carbocyclic radical having a single ring (e.g., phenyl) or two condensed rings (e.g., naphthyl), which can optionally be substituted with hydroxyl, lower alky, chloro, and/or cyano.

The term "effective amount" refers to the amount of a compound of formula (I) that will restore immune function to normal levels, or increase immune function above normal levels in order to eliminate infection.

The term "enantiomers" refers to a pair of stereoisomers that are non-superimposable mirror images of each other. A mixture of a pair of enantiomers, in a 1:1 ratio, is a "racemic" mixture.

The term "heterocycle" refers to a monovalent saturated or unsaturated carbocyclic radical having at least one hetero atom, such as N, O or S, within the ring each available position of which can be optionally substituted, independently, with, e.g., hydroxy, oxo, amino, imino, lower alkyl, bromo, chloro and/or cyano. Included within this class of substituents are purines, pyrimidines.

The term "immunomodulators" refers to natural or synthetic products capable of modifying the normal or aberrant immune system through stimulation or suppression.

The term "isomers" refers to different compounds that have the same formula. "Stereoisomers" are isomers that differ only in the way the atoms are arranged in space.

The term "L-configuration" is used throughout the present invention to describe the chemical configuration of the ribofuranosyl moiety of the compounds that is linked to the nucleobases. The L-configuration of the sugar moiety of compounds of the present invention contrasts with the D-configuration of ribose sugar moieties of the naturally occurring nucleosides such as cytidine, adenosine, thymidine, guanosine and uridine.

The term "lower alkyl" refers to methyl, ethyl, n-propyl, isopropyl, n-butyl, t-butyl, 1-butyl or n-hexyl. This term is further exemplified to a cyclic, branched or straight chain from one to six carbon atoms.

The term "monocyclic" refers to a monovalent saturated carbocyclic radical having at least one hetero atom, such as O, N, S, Se or P, within the ring, each available position of which can be optionally substituted, independently, with a sugar moiety or any other groups like bromo, chloro and/or cyano, so that the monocyclic ring system eventually aromatized [e.g., Thymidine].

The term "nucleoside" refers to a compound composed of any pentose or modified pentose moiety attached to a specific position of a heterocycle or to the natural position of a purine (9-position) or pyrimidine (I-position) or to the equivalent position in an analog, including especially both D- and L- forms of nitrogenous monocyclic heterocycles depicted in FIG. 1.

The term "C-nucleosides" is used throughout the specification to describe the linkage type that formed between the ribose sugar moiety and the heterocyclic base. In C-nucleosides, the linkage originates from the C-1 position of the ribose sugar moiety and joins the carbon of the heterocyclic base. The linkage that forms in C-nucleosides is carbon-to-carbon type.

The term "D-nucleosides" refers to nucleoside compounds that have a D-ribose sugar moiety (e.g., Adenosine). The term "L-nucleosides" refers to nucleoside compounds that have an L-ribose sugar moiety.

The term "N-nucleosides" is used throughout the specification to describe the linkage type that formed between the ribose sugar moiety and the heterocyclic base. In N-nucleosides, the linkage originates from the C-1 position of the ribose sugar moiety and joins the nitrogen of the heterocyclic base. The linkage that forms in N-nucleosides is carbon to nitrogen type.

The term "nucleotide" refers to a phosphate ester substituted on the 5-position of a nucleoside.

The term "pharmaceutically acceptable salts" refers to any salt derived from inorganic and organic acids or bases.

The term "protecting group" refers to a chemical group that is added to, oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The term "pyrimidine" refers to nitrogenous monocyclic heterocycles depicted in FIG. 1.

The term "tumor" refers broadly to all manner of autonomous morbid growth of tissue that may or may not become malignant, including all manner of neoplasms and cancers.

The terms "treating" or "treatment" of a disease refers to executing a protocol, which may include administering one or more drugs to a patient, in an effort to alleviate signs or symptoms of the disease. Thus, "treating" or "treatment" do not require complete alleviation of signs or symptoms, do not require a cure, and specifically include protocols which have only marginal effect on the patient.

Combinations and Methods

Contemplated combinations in one aspect of the present invention generally include a primary or "first" drug and another or "second" drug, and contemplated methods involve selecting and combining the first and second drugs in combination therapies. In preferred embodiments, a disease is identified which is known to produce an abnormality in at least one cytokine in a patient. The first drug is selected from among those compounds demonstrated to treat the disease at a monotherapeutic dosage, and the second drug, which may be a bimodal nucleoside modulator as herein described, is selected from among those compounds known to exacerbate the very abnormality produced by the disease when administered within a given dosage range. The first drug is then administered at less than the monotherapeutic dosage and the second drug is administered in a dosage outside the dosage range that exacerbates the abnormality. Since the second drug has a bimodal activity with respect to at least some of the cytokines of interest, the combination is still effective to treat the disease, and administration of the second drug allows reduction in the administered dosage of the primary or first drug.

Examples of primary drugs contemplated to be effective in combination with a modulator selected from FIG. 1 are anti-viral agents such as interferon, including but not limited to interferonα and γ, Ribavirin, acyclovir, and AZT™; anti-fungal agents such as tolnaftate, Fungizone™, Lotrimin™, Mycelex™, Nystatin and Amphoteracin; anti-parasitics such as Mintezol™, Niclocide™, Vermox™, and Flagyl™, bowel agents such as Immodium™, Lomotil™ and Phazyme™; anti-tumor agents such as interferonαand γ, Adriamycin , Cytoxan™, Imuran™, Methotrexate, Mithracin™, Tiazofurin™, Taxol™; dermatologic agents such as Aclovate™, Cyclocort™, Denorex™, Florone™, Oxsoralen™, coal tar and salicylic acid; migraine preparations such as ergotamine compounds; steroids and immunosuppresants not listed above, including cyclosporins, Diprosone™, hydrocortisone; Floron™, Lidex™, Topicort and Valisone; and metabolic agents such as insulin, and other drugs which may not nicely fit into the above categories, including cytokines such as IL2,IL4,IL6,IL8, IL10 and IL12.Especially preferred primary drugs are AZT, 3TC, 8-substituted guanosine analogs, 2,3-dideoxynucleosides, interleukin II, interferons such as IαB-interferons, tucaresol, levamisole, isoprinosine and cyclo-lignans.

Examples of secondary drugs contemplated to be effective in the invention are D-and L- forms of monocyclic nucleo-sides corresponding to Formula 1. Other nucleoside and non-nucleoside compounds effective in the invention are readily identified through screening of such compounds in vitro for effect on IL-2,TNF-α, IFN-γ, IL-4 and IL-5 as described in PCT/US97/00600.

Formula 1 compounds are:

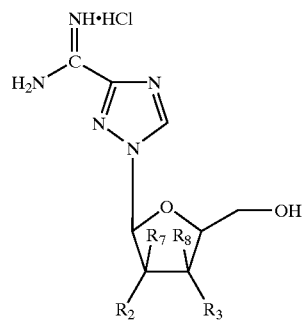

wherein:

$R_2$, $R_3$, $R_7$ and $R_8$ are independently selected from H, OH, CN, $N_3$, halogens, $CH_2OH$, $NH_2$, $OCH_3$, $NHCH_3$, $ONHCH_3$, $SCH_3$, SPh, alkenyl, lower alkyl, lower alkyl amines or substituted heterocycles.

It is contemplated that when $R_2$ =$R_3$ =H, then $R_7$ and R8 are hydrogen atoms or nothing. It is preferred that when, in compounds of Formula 1,$R_7$ =$R_8$ =H that $R_2$ =$R_3$ =OH.

In another aspect of the invention, an abnormality reflected in increased response in one group of cytokines is treated by administering a nucleoside or other compound that increases response in another group of cytokines. Thus, for example, a common rapid onset type of allergy results in an abnormally elevated Th2 response. The abnormality is treated by administering Ribavirin at between 600 mg/day and 1,000 mg/day (for a typical adult), at which dose the Th1 response is induced. The treatment is effective because Th1 and Th2 have a teeter-totter type relationship in this instance, such that the Th2 response is suppressed.

In yet another aspect of the invention, a patient is prophylactically treated by administering a nucleoside or other compound that selectively reduces Th1 activity without significantly reducing Th2 activity. The prophylaxis can, for example, prepare the patient for organ or tissue transplant, or for anticipated contact with allergens.

In yet another aspect of the invention, a nucleoside or other compound is administered to a patient at a dose that reduces the patient's GTP pool to a degree that selectively reduces one of the Th1 or Th2 responses without significantly reducing the other response. Controlled release dosage forms are particularly contemplated to achieve that result, especially formulations which maintain the dose of the compound in the serum within a desirable range. In the case of Ribavirin, for example, the serum level should be maintained between about 2 $\mu$M and about 5 $\mu$M. In terms of delivery rates, a controlled release formulation may advantageously have an in vitro dissolution rate when measured by the USP Paddle Method at 100 rpm at 900 ml aqueous buffer (pH between 1.6 and 7.2) between about 15% and 40% by weight of the compound after 1 hour, between about 30%. and about 50% by weight of the compound after 2 hours, about 50% and 70% by weight of the compound after 4 hours, between about 60% and about 80% by weight of the compound after 6 hours

Uses

It is contemplated that the claimed combinations will be used to treat a wide variety of conditions, and in fact any condition which responds positively to administration of one or more such combinations. Among other things, it is specifically contemplated that such combinations may be used to treat an infection, an infestation, a tumor, hypersensitivity or an autoimmune disease.

Infections contemplated to be treated with the compounds of the present invention include respiratory syncytial virus (RSV), hepatitis B virus (HBV), hepatitis C virus (HCV), herpes simplex type 1 and 2,herpes genitalis, herpes keratitis, herpes encephalitis, herpes zoster. human immunodeficiency virus (HIV), influenza A virus, hantann virus (hemorrhagic fever), human. papilloma virus (HPV), measles and fungus. It is especially contemplated that combinations claimed herein will be useful in treating chronic viral and bacterial infections, including HIV, Tuberculosis, leprosy and so forth.

Infestations contemplated to be treated with the compounds of the present invention include intracellular protozoan infestations, as well as helminth and other parasitic infestations. Again, it is especially contemplated that combinations claimed herein will be useful in treating chronic infestations.

Tumors contemplated to be treated include those caused by a virus, and the effect may involve inhibiting the transformation of virus-infected cells to a neoplastic state, inhibiting the spread of viruses from transformed cells to other normal cells and/or arresting the growth of virus-transformed cells.

Hypersensitivities contemplated to be treated include all types of allergies, including IgE and IgG allergies, hyper IgE syndrome, and dermatic conditions such as atopic dermatitis. It is also contemplated that claimed combinations can be used to treat transplant rejection, (graft vs. host disease) and implant reactions.

Autoimmune diseases can be classified as either non-organ-specific or organ-specific. Non-organ-specific autoimmune diseases include rheumatoid arthritis, gout and gouty arthritis, Systemic Lupus Erythematosus (SLE), Sjogren syndrome, scieroderma, polymyositis and dermomyositis, ankylosing spondylitis, and rheumatic fever. Organ-specific autoimmune diseases are known for virtually every organ, including insulin-dependent diabetes, thyroid diseases (Graves disease and Hashimoto thyroiditis), Addison disease, and some kidney and lung diseases including allergy and asthma, multiple sclerosis, myasthenia gravis, uveitis, psoriasis, forms of hepatitis and cirrhosis, celiac disease, inflammatory bowel disease, and some types of male and female infertility. Autoimmune processes may also be stimulated by viral infections including the HIV virus, may result from rejection of transplantation, and may accompany certain tumors, or be precipitated by exposure to some chemicals.

It is also contemplated that an abnormality reflected in increased response in one group of cytokines can be treated by administering a nucleoside that increases response in another group of cytokines. Thus, for example, since common IgE allergies are associated with a predominantly Th2 response, allergies can be treated with Ribavirin, which increases Th1 response at low dosages of about 500 mg/day to about 1,000 mg/day.

In yet another aspect of the invention, a patient is prophylactically treated by administering a compound that selectively reduces Th1 activity without significantly reducing Th2 activity. The prophylactic treatment may be to reduce expected undesirable effects from an upcoming event, such as an organ or tissue transplant, or to reduce symptoms from an expected pulmonary insult, as from the onset of increase in airborne pollen levels in spring.

Synthesis

Synthesis of compounds according to Formula 1 was set forth in co-pending PCT application PCTIUS97/00600 and are herein incorporated by reference.

Administration

With respect to the dosage of Formula 1,it is contemplated that various alternative dosages are also appropriate, including dosages between 0.5 mg/kg and 0.1 mg/kg and less, but also dosages between 0.5 and 1.0 Omg/kg and more. In general, the appropriate dosage will depend on multiple parameters, including the type of virus infection, the stage of the virus infection, the desired plasma concentration of the compounds of Formula 1,the duration of the treatment, etc. For example, while treatment success may be achieved with some viral infections at relatively low plasma concentrations of the compounds of Formula 1,other viral infections may require relatively high dosages.

In still further alternative aspects of the inventive subject matter, Formula 1 may be replaced with Levovirin™, depending on the particular type of viral infection or stage of a particular viral infection. For example, while one type of viral infection may respond well to treatment with Formula 1,other types of viral infections may be more responsive to treatment with Levovirin™. It is further contemplated that a treatment of a viral infection need not be limited to Levovirin™ or the carboxamidine compound (Formula 1), but alternative treatments may include mixtures of Levovirin™ and the carboxamidine compound. The ratio of Levovirin™ to Formula 1 compounds may thereby vary among various types of viral infections or even during various stages of a single type of viral infection.

It should further be appreciated that the Formula 1 compound may be combined with additional pharmaceutically active substances to assist in the treatment of the viral infections. Contemplated additional pharmaceutically active substances include antiviral agents and immune modulator substances. For example, antiviral agents are protease inhibitors, or nucleotide and nucleoside analogs, and immune modulator substances may include cytokines.

Although not wishing to be bound to any particular theory, it is contemplated that the administration of the Formula 1 compound is correlated with an increase of the Th1 response relative to the Th2 response in a patient, and it is especially contemplated that the relative increase of the Th1 response to the Th2 response is due to an absolute increase in the Th1 response. The cytokine levels may thereby be increased individually or collectively. For example, it is contemplated that administration of the Formula 1 compound to activated human PBMCs may result in a mean peak increase of the IL-2 level of at least 70%(by weight) over an activated control level. Alternatively, it is contemplated that administration of the Formula 1 compound to activated human PBMCs may result in a mean peak increase of the IFN-γ level of at least 20%(by weight) over an activated control level, or in a mean peak increase of the TNF-α level of at least 50%(by weight) over an activated control level. In another example, it is contemplated that the increase in the Th1 response may comprises a mean peak increase over an activated control level in IL-2, IFN-γ, and TNF-α of 70%(weight), 20%(weight), and 50%(weight), respectively.

Administration of compounds according to the present invention may take place orally, parenterally (including subcutaneous injections, intravenous, intramuscularly, by intrastemal injection or infusion techniques), by inhalation spray, or rectally, topically and so forth, and in dosage unit formulations containing conventional non-toxic pharmaceutically acceptable carriers, adjuvants and vehicles.

It is contemplated that compounds according to the present invention can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in patients.

In certain pharmaceutical dosage forms, the pro-drug form of administered compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to a targeted site within the host organism or patient to maximize the intended effect of the compound.

In addition, compounds included in combinations according to the present invention may be administered separately or together, and when administered separately this may occur in any order. The amounts of the active ingredient(s) and pharmaceutically active agent(s) and the relative timings of administration will be selected in order to achieve the desired combined therapeutic effect.

Administration routes of compounds according to the present invention may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare therapies according to the present invention, a therapeutically effective amount of a compound is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

It will also be appreciated that in general, the most preferred uses according to the present invention are those in which the active compounds are relatively less cytotoxic to the non-target host cells and relatively more active against the target. In this respect, it may also be advantageous that L-nucleosides may have increased stability over D-nucleosides, which could lead to better pharmacokinetics. This result may attain because L-nucleosides may not be recognized by enzymes, and therefore may have longer half-lives.

Thus, therapies have been disclosed which employ nucleosides and other compounds to selectively modulate Th1 and Th2 responses relative to each other in the treatment of disease. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. A method of selectively modulating Th1 and Th2 responses in a peripheral blood mononuclear cell of a patient infected with a virus comprising: identifying a patient in need of treatment for a viral infection; administering a compound according to formula 1 to the patient

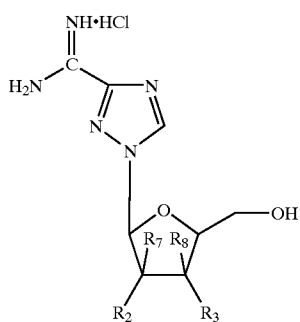

Formula 1 wherein $R_2$, $R_3$, $R_7$ and $R_8$ are independently selected from H, OH, CN, $N_3$, halogens, $CH_2OH$, $NH_2$, $OCH_3$, $NHCH_3$, $ONHCH_3$, $SCH_3$, SPh, alkenyl, lower alkyl, lower alkyl amines or substituted heterocycles; and administering the compound to the peripheral blood mononuclear cell at a concentration effective to selectively modulate the Th1 and Th2 responses relative to each other.

2. The method of claim 1 wherein the viral infection is selected from the group consisting of an HIV infection, an HCV infection, and a HBV infection.

3. The method of claim 1 wherein the step of administering increases a Th1 response relative to a Th2 response in the peripheral blood mononuclear cell.

4. The method of claim 3 wherein the Th1 response increases.

5. The method of claim 4 wherein the increase in the Th1 response comprises a mean peak increase over an activated control level in IL-2 of at least 20%(by weight).

6. The method of claim 4 wherein the increase in the Th1 response comprises a mean peak increase over an activated control level in IFN-γ of at least 75%(by weight).

7. The method of claim 4 wherein the increase in the Th1 response comprises a mean peak increase over an activated control level in TNF-α of at least 50%(by weight).

8. The method of claim 4 wherein the increase in the Th1 response comprises a mean peak increase over an activated control level in IL-2, IFN-γ, and TNF-α of 42%(mole), 125%(mole), and 72%(mole), respectively.

9. The method of claim 1 wherein the step of administering comprises in vivo administration.

10. The method of claim 1 wherein the step of administering comprises oral administration.

11. The method of claim 1 wherein the step of administering comprises injection of the L-ribonucleoside.

12. The method of claim 1 wherein the step of administering comprises administering the compound in a dose between 0.1 mg per kg of body weight of the patient and 1.0 mg per kg of body weight of the patient.

* * * * *